United States Patent [19]

Curtis et al.

[11] Patent Number: 5,252,331
[45] Date of Patent: Oct. 12, 1993

[54] LESS IRRITATING SHAVING MATERIAL

[75] Inventors: Austin W. Curtis, Detroit, Mich.; Lorenzo Freeman, 4211 Avery, Detroit, Mich. 48208

[73] Assignee: Lorenzo Freeman, Detroit, Mich.

[21] Appl. No.: 847,699

[22] Filed: Mar. 5, 1992

[51] Int. Cl.$^5$ .............................................. A61K 7/15
[52] U.S. Cl. ..................................... 424/401; 424/73; 424/195.1
[58] Field of Search ........................ 424/401, 73, 195.1

[56] References Cited

U.S. PATENT DOCUMENTS

| | | | |
|---|---|---|---|
| 3,810,996 | 5/1974 | Sutliff et al. | 514/783 |
| 3,852,417 | 12/1974 | McLaughlin | 424/73 |
| 4,255,452 | 3/1981 | Veney | 514/775 |
| 4,369,180 | 1/1983 | Mihalouits | 424/195.1 |
| 4,395,424 | 7/1983 | Veney | 514/772 |
| 4,505,902 | 3/1985 | Millard | 424/195.1 |
| 4,525,344 | 6/1985 | Tutsky | 424/73 |
| 4,761,278 | 8/1988 | Lewis et al. | 424/73 |
| 4,775,530 | 10/1988 | Perricone | 424/73 |
| 4,911,925 | 3/1990 | Shatking et al. | 424/401 |
| 4,944,939 | 8/1990 | Moore | 424/73 |
| 4,986,986 | 1/1991 | Roth | 424/195.1 |
| 4,994,265 | 2/1991 | White | 424/73 |
| 5,002,680 | 3/1991 | Schmidt et al. | 252/132 |
| 5,002,760 | 3/1991 | Katzev | 514/844 |
| 5,034,221 | 8/1991 | Rosen | 424/73 |
| 5,063,062 | 11/1991 | Greenspan et al. | 424/401 |

FOREIGN PATENT DOCUMENTS

| | | |
|---|---|---|
| 343342 | 10/1921 | Fed. Rep. of Germany . |
| 2268513 | 11/1975 | France . |
| 2416010 | 8/1979 | France . |
| 0091146 | 10/1978 | Japan . |
| 144874 | 6/1920 | United Kingdom . |

Primary Examiner—Thurman K. Page
Assistant Examiner—Amy Hulina
Attorney, Agent, or Firm—Dykema Gossett

[57] ABSTRACT

An improved shaving cream is disclosed which contains an effective amount of olive oil. Preferably, the shaving cream compositions contains aloe vera and mineral oil. Other additives can also be incorporated into the shaving cream composition. The improved shaving cream reduces the amount of irritation to the skin due to shaving and soothes any irritation to the skin which may occur. The improved shaving cream, especially the improved shaving cream containing both olive oil and aloe vera, minimizes the occurrence of ingrown hairs resulting from shaving and reduces the severity of any ingrown hairs that do occur. This shaving cream is, therefore, especially useful for individuals prone to ingrown hairs and other skin problems normally associated with shaving.

10 Claims, No Drawings

LESS IRRITATING SHAVING MATERIAL

BACKGROUND OF THE INVENTION

This invention relates to a shaving cream containing olive oil. More specifically, this invention relates to an improved shaving cream containing olive oil which reduces the number and severity of ingrown hairs resulting from shaving facial or other hair on the body.

Shaving a particular area of skin has typically caused some irritation to the area, and has often resulted in ingrown hairs. This is particularly true for people of African or Mediterranean descent. Several types of shaving compositions are known which attempt to reduce the amount of irritation due to shaving. Some shaving compositions may include an aloe vera product to soothe the skin. Further, other shaving products include various ingredients which decrease the amount of sliding friction between the razor blade and the skin, thereby reducing the amount of irritation to the skin. In general, however, the known shaving products have not successfully addressed the problem of ingrown hairs due to shaving.

SUMMARY OF THE INVENTION

A disclosed embodiment of the present invention includes an olive oil-containing shaving cream and a method of applying an olive oil-containing shaving cream to an area to be shaved, whereby the olive oil reduces the amount of irritation to the skin due to the shaving. Further, the olive oil is preferably combined with an aloe vera product such that the olive oil reduces the amount of irritation, and the aloe vera product treats any irritation that does occur. This inventive shaving cream also reduces the number of ingrown hairs, and other skin problems that often result from shaving. And, for ingrown hairs that do occur, their severity is significantly reduced. The shaving cream of this invention is, therefore, especially suited for use by individuals who are especially susceptible to ingrown hairs and other skin and skin-related problems associated with shaving.

In a further preferred embodiment of this invention the shaving composition includes olive oil, mineral oil, and aloe vera. Conventional additives generally used in shaving creams and similar pharmaceutical-type products can also added to the compositions of the present invention. Such conventional additives can include, for example, other lubricants, binders, waxes, lotions, emulsifiers, surfactants, inhibitors, emollients, antifungal agents, colorings, fragrances, and the like.

These and other objects and features of the present invention can be best understood from the following specification.

DETAILED DESCRIPTION OF THE PREFERRED EMBODIMENTS

An improved shaving cream containing olive oil as a significant ingredient has been found. The olive oil appears to act as an effective lubricant in reducing the amount of irritation from shaving a particular area of skin. In addition to its lubricating effect, the olive oil, especially when combined with aloe vera, appears to reduce the number of ingrown hairs resulting from shaving and to reduce the severity of ingrown hairs that do occur. Thus, a method of shaving according to the present invention includes the application of olive oil, and preferably olive oil and aloe vera, to an area to be shaven, and then shaving that area. The shaving cream and method of shaving of the present invention can be used to remove unwanted hair on the facial area, on the legs, in the underarm area, as well as other parts of the body (such as, for example, in preparation for surgery).

As noted above, olive oil is preferably used in combination with an aloe vera product, and even more preferably in combination with an aloe vera product and a mineral oil. In other embodiments, lanolin or vitamin E containing materials can be incorporated into the present shaving cream compositions. Also as noted above, other conventional additives can be added to the shaving compositions of the present invention. Such conventional additives can include, for example, other lubricants, binders, waxes, emulsifiers, lotions, surfactants, inhibitors, emollients, antifungal agents, colorings, fragrances, and the like. The materials are mixed into a deionized water base along with any other desired ingredients. The resulting shaving cream reduces irritation due to shaving and further soothes any irritations that do occur. The resulting shaving cream also reduces the number of ingrown hairs resulting from shaving and further reduces the severity of the ingrown hairs resulting from shaving.

The shaving cream compositions of the present invention contain an effective amount of olive oil, preferably refined olive oil. An effective amount of olive oil, for purposes of this invention, is an amount which significantly reduces the amount or degree of irritation during normal shaving events and/or the amount which significantly reduces the incidence or severity of ingrown hairs caused by normal shaving events. Generally, the compositions of the present invention will contain 1 to 25 parts by weight olive oil and 100 parts by weight water. Preferably, the compositions of the present invention contain 5 to 10 parts by weight olive oil and 100 parts by weight water. One preferred shaving cream composition will also contain 0.1 to 10 parts by weight aloe vera in either the liquid or cream form. Another preferred shaving cream composition will, in addition to the above amounts of olive oil, water, and aloe vera, also contain 10 to 40 parts by weight mineral oil. Still another preferred shaving cream composition will, in addition to the above ingredients, contain about 0.1 to 5 parts by weight lanolin or Vitamin E linoleate. Vitamin E linoleate contains vitamin E which is thought to be beneficial in healing skin abrasions and the like. It also generally preferred that the shaving cream compositions also contain an effective amount of an antifungal agent such as, for example, propylparaben or methylparaben. Generally, an effective amount of such an antifungal agent would be about 0.01 to 2 parts by weight in the above compositions.

One especially preferred composition suitable for shaving whereby the incidence of ingrown hairs is significantly reduced, contains:

1 to 25 parts by weight olive oil;
0.1 to 10 parts by weight aloe vera;
10 to 40 parts by weight mineral oil;
0.1 to 10 parts by weight self-emulsifying wax;
0.1 to 10 parts by weight petrolatum;
0.1 to 10 parts by weight lanolin or Vitamin E linoleate;
0.05 to 5 parts cetyl alcohol; and
100 parts by weight water.

Another especially preferred composition suitable for shaving contains:

5 to 15 parts by weight olive oil;

2 to 5 parts by weight aloe vera;
25 to 35 parts by weight mineral oil;
4 to 8 parts by weight self-emulsifying wax;
4 to 8 parts by weight petrolatum;
4 to 8 parts by weight lanolin or vitamin E linoleate;
1 to 2 parts cetyl alcohol; and
100 parts by weight water.

Either of these especially preferred compositions may also contain an effective amount of an antifungal agent such as, for example, propylparaben or methylparaben.

Generally the shaving cream compositions of this invention are in the form of a cream (i.e., a relatively high viscosity liquid) suitable for application, for example, to the face. Aerosol shaving cream compositions containing olive oil in accordance with the present invention can be prepared by employing suitable propellants and packaging techniques.

The following examples are intended to illustrate the invention and not to limit the invention.

EXAMPLE 1

Approximately one hundred pounds of a shaving cream was prepared using the following procedure. First, an oil phase was formed by mixing the following ingredients at room temperature:

| INGREDIENT | SPECIFIC GRAVITY | AMOUNT |
|---|---|---|
| Refined olive oil | 0.915-0.920 | 6 pounds |
| Mineral oil | 0.875-0.905 | 19 pounds |
| Self-emulsifying wax | 0.95 | 3.0 pounds |
| Petrolatum | 0.820-0.865 | 4 pounds |
| Lanolin | 0.970-0.973 | 3 pounds |
| Cetyl alcohol | 1.4283 | 1 pound |
| Propylparaben | — | 45.4 grams |
| Methylparaben | — | 22.5 grams |

The mineral oil used was a white mineral oil with the tradename Drakeol 32 which is available from Penreco (a division of Pennzoil Products Company). The self-emulsifying wax used was Polawax TM available from Croda, Inc. The petrolatum was white petrolatum known as "Penreco Snow" from Penreco. The lanolin used was from Rita Corporation. The cetyl alcohol used was from Sherex Corporation. The antifungal agents (propylparaben and methylparaben) were obtained from Tri-K Industries.

The aqueous phase was prepared by blending the following ingredients together at room temperature:

| INGREDIENT | SPECIFIC GRAVITY | AMOUNT |
|---|---|---|
| Deionized water | 1.0 | 62 pounds |
| Aloe vera liquid | ca. 0.9 | 2 pounds |

The oil and aqueous phases were then separately heated to about 60° C. The aqueous phase was then added to the oil phase while stirring. A small amount of fragrance at about 35° C. was then added to the blended shaving cream composition. The final shaving cream composition was then allowed to cool to room temperature. The consistency of the composition was suitable for use as a shaving cream.

EXAMPLE 2

A similar shaving cream composition was prepared from an oil phase containing olive oil (6 pounds), mineral oil (21 pounds), self-emulsifying wax (3 pounds), petrolatum (5 pounds), cetyl alcohol (1 pound), vitamin E linoleate (0.1 pounds), propylparaben (0.1 pounds), and methylparben (0.15 pounds). The vitamin E linoleate (specific gravity of 0.93) is a vegetable derived product containing vitamin E. Except for the vitamin E linoleate, the materials used were the same as in Example 1. When combined with an aqueous phase containing water (62 pounds) and aloe vera (2 pounds) in a manner similar to Example 1, a shaving cream composition suitable for use in shaving was obtained.

The shaving cream compositions in Examples 1 and 2 were used for shaving both facial hair (male subjects) and leg hair (female subjects). Both compositions were successful in reducing the amount of irritation and skin damage or abrasion from shaving in both male and female subjects. Use of the compositions of Examples 1 and 2 resulted in reduced number of ingrown hairs and in the severity of ingrown hairs which did result.

Although specific embodiments have been disclosed, a worker of ordinary skill in the art would recognize that certain modifications would fall within the scope of this invention. For that reason, the following claims should be studied in order to determine the scope and content of this invention.

We claim:

1. A composition suitable for shaving whereby the incidence of ingrown hairs is significantly reduced, said composition comprising
   1 to 25 parts by weight olive oil;
   0.1 to 10 parts by weight aloe vera;
   10 to 40 parts by weight mineral oil;
   0.1 to 10 parts by weight self-emulsifying wax;
   0.1 to 10 parts by weight petrolatum;
   0.05 to 5 parts cetyl alcohol; and
   100 parts by weight water.

2. A composition as defined in claim 1, wherein the composition also contains an effective amount of an antifungal agent.

3. A composition as defined in claim 2, wherein the antifungal agent is 0.01 to 2 parts by weight propylparaben or methylparaben.

4. A composition as defined in claim 1, wherein the composition also contains vitamin E.

5. A composition as defined in claim 1, wherein the composition contains
   5 to 15 parts by weight olive oil;
   2 to 5 parts by weight aloe vera;
   25 to 35 parts by weight mineral oil;
   4 to 8 parts by weight self-emulsifying wax;
   4 to 8 parts by weight petrolatum;
   1 to 2 parts cetyl alcohol; and
   100 parts by weight water.

6. A shaving cream composition as defined in claim 5, wherein the composition is in the form of an aerosol containing propellants.

7. A composition as defined in claim 5, wherein the composition also contains an effective amount of an antifungal agent.

8. A composition as defined in claim 7, wherein the antifungal agent is 0.01 to 2 parts by weight propylparaben or methylparaben.

9. A composition as defined in claim 7, wherein the composition also contains vitamin E.

10. A shaving cream composition as defined in claim 1, wherein the composition is in the form of an aerosol containing propellants.

* * * * *

UNITED STATES PATENT AND TRADEMARK OFFICE
CERTIFICATE OF CORRECTION

PATENT NO.  :   5,252,331

DATED       :   October 12, 1993

INVENTOR(S) :   Austin W. Curtis and Lorenzo Freeman

It is certified that error appears in the above-identified patent and that said Letters Patent is hereby corrected as shown below:

On the title page, item [75]: Delete "4211 Avery," after Lorenzo Freeman.

Signed and Sealed this

Thirtieth Day of May, 1995

Attest:

BRUCE LEHMAN

Attesting Officer        Commissioner of Patents and Trademarks